United States Patent [19]
Jacobsen et al.

[11] Patent Number: 5,859,061
[45] Date of Patent: Jan. 12, 1999

[54] BIS-SULFONAMIDES HYDROXAMIC ACIDS AS MMP INHIBITORS

[75] Inventors: Eric Jon Jacobsen, Plainwell; Louis L. Skaletzky, Kalamazoo, both of Mich.

[73] Assignee: Pharmacia & Upjohn Company, Kalamazoo, Mich.

[21] Appl. No.: 5,310

[22] Filed: Jan. 9, 1998

Related U.S. Application Data

[60] Provisional application No. 60/037,625, Jan. 17, 1997.
[51] Int. Cl.$^6$ ................................................. A01N 37/28
[52] U.S. Cl. .......................................... 514/575; 562/623
[58] Field of Search ............................ 592/623; 514/575

[56] References Cited

U.S. PATENT DOCUMENTS

| | | | |
|---|---|---|---|
| 5,506,242 | 4/1996 | MacPherson et al. | 514/336 |
| 5,552,419 | 9/1996 | MacPherson et al. | 514/357 |

FOREIGN PATENT DOCUMENTS

| | | | |
|---|---|---|---|
| 0606046 A1 | 7/1994 | European Pat. Off. | C07D 213/42 |
| 95/35275 | 12/1995 | WIPO | C07C 311/06 |
| 95/35276 | 12/1995 | WIPO | C07C 311/19 |
| 96/00214 | 1/1996 | WIPO | C07D 213/42 |
| 96/27583 | 9/1996 | WIPO | C07C 311/29 |

OTHER PUBLICATIONS

U.S. application Ser. No. 60/029,585, M. Warpehoski, et al., Oct. 23, 1996.

*Primary Examiner*—Porfirio Nazario-Gonzalez
*Assistant Examiner*—Brian J. Davis
*Attorney, Agent, or Firm*—Lucy X. Yang

[57] ABSTRACT

The present invention provides a compound of formula I

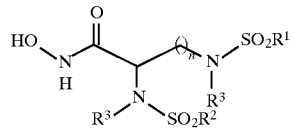

or pharmaceutically acceptable salts thereof wherein $R^1$ and $R^2$ are the same or different and are $C_{1-10}$ alkyl, phenyl, hetero-aryl, or phenyl substituted with $C_{1-4}$ alkyl, $OR^3$, $NHR^3$, $CONHR^3$, $NHCOR^3$, or halo; wherein $R^3$ is H, or $C_{1-4}$ alkyl; and n is 1, 2, 3, 4, 5, or 6. The compounds are inhibitors of matrix metalloproteinases involved in tissue degradation.

13 Claims, No Drawings

BIS-SULFONAMIDES HYDROXAMIC ACIDS AS MMP INHIBITORS

CROSS-REFERENCE TO RELATED APPLICATION

This application claims the benefit of the following provisional application: U.S. Ser. No. 60/037,625, filed Jan. 17, 1997, under 35 USC 119(e)(i).

FIELD OF THE INVENTION

The present invention relates to novel bis-sulfonamides hydroxamic acids, to pharmaceutical compositions containing them, and to the method of using such compounds. Particularly, the compounds of the invention are inhibitors of matrix metalloproteinases involved in tissue degradation.

BACKGROUND OF THE INVENTION

Loss of connective tissue integrity occurs in many disease processes, including osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, and other diseases related to connective tissue degradation. Although there is a high incidence of these diseases in the developed world, there is no treatment that prevents the tissue damage that occurs. Considerable lines of scientific evidence indicate that uncontrolled connective matrix metalloproteinase (MMPs) activity is responsible for the damage, and as a consequence the inhibition of these enzymes has become the target for therapeutic intervention (see Matrisian, L. M., Bases, Vol. 14, pp 445–463, (1992); Emonard, H. et al., Cellular and molecular Biology, Vol. 36, pp 131–153, (1990); Docherty, A. J. P. et al., Annals of the Rheumatic, Vol. 49, pp 469–479, (1990).

Hydroxamic acid derivatives are a class of known therapeutically active MMPs inhibitors and there are numerous references in the art disclosing a variety of hydroxamic acid derivatives. For example, European Patent Publication 0,606,046 A1 discloses arylsulfonamido-substituted hydroxamic acids useful as matrix metalloproteinase inhibitors. International Publication Nos. WO95/35275 and WO95/35276 disclose sulfonamide hydroxamic acid and carboxylic acid derivatives useful as matrix metalloproteinases inhibitors. All these references relate to mono-sulfonamide hydroxamic acids. The compounds of this invention are novel and distinct from all other sulfonamide hydroxamic acids in that it provides bis-sulfonamide hydroxamic acids.

The compounds of the present invention have unexpected superior activity in inhibiting various enzymes from the matrix metalloproteinase family such as collagenase, stromelysin, and gelatinase, and hence are useful for the treatment of matrix metallo endoproteinase diseases such as osteoporosis, tumor metastasis (invasion and growth), periodontitis, gingivitis, corneal ulceration, dermal ulceration, gastric ulceration, inflammation, and other diseases related to connective tissue degradation.

INFORMATION DISCLOSURE

The following patent publications disclose sulfonamide hydroxamic acids as matrix metalloproteinase inhibitors:

European Patent Publication 0,606,046 A1 discloses arylsulfonamido-substituted hydroxamic acids useful as matrix metalloproteinase inhibitors.

International Publication No. WO 95/35275 and WO 95/35276 disclose hydroxamic acid and carboxylic acid derivatives useful as matrix metalloproteinases inhibitors.

U.S. patent application, Ser. No. 60/029,585 discloses α-amino sulfonyl hydroxamic acids useful as matrix metalloproteinases inhibitors.

SUMMARY OF THE INVENTION

The present invention provides a compound of formula I

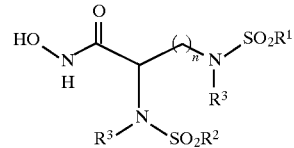

or pharmaceutically acceptable salts thereof wherein
$R^1$ and $R^2$ are the same or different and are
  a) $C_{1-10}$ alkyl,
  b) phenyl,
  c) hetero-aryl, or
  d) phenyl substituted with $C_{1-4}$ alkyl $OR^3$, $NHR^3$, $CONHR^3$, $NHCOR^3$, $SO_2NHR^3$, or halo;
$R^3$ is
  a) H, or
  b) $C_{1-4}$ alkyl;
and n is 1, 2, 3, 4, 5, or 6.

The compounds of the present invention inhibit various enzymes from the matrix metalloproteinase family such as collagenase, stromelysin, and gelatinase, and hence are useful for the treatment of matrix metallo endoproteinase diseases.

DETAILED DESCRIPTION OF THE INVENTION

For the purpose of the present invention, the carbon content of various hydrocarbon containing moieties is indicated by a prefix designating the minimum and maximum number of carbon atoms in the moiety, i.e., the prefix $C_{i-j}$ defines the number of carbon atoms present from the integer "i" to the integer "j", inclusive.

Thus, the term "$C_{1-10}$ alkyl" and "$C_{1-4}$ alkyl" refer to alkyl of one to six or one to four carbon atoms, respectively such as, for example, methyl, ethyl, propyl, butyl, pentyl, hexyl, etc., and their isomeric forms thereof, preferably an alkyl group of $R^1$ or $R^2$ having one to four carbon atoms, and an alkyl group of $R^3$ having one to two carbon atoms.

The term "hetero-aryl" refers to a 5 to 10 membered unsaturated heterocyclic moiety having one or more atoms selected from the group consisting of oxygen, nitrogen, and sulfur such as; for example, pyridyl, pyrimidinyl, pyridazinyl, quinolyl, quinazolinyl, imidazolyl, pyrazolyl, thiazolyl, indolyl, isoindolyl, furanyl, thienyl, pyrrolyl, and purinyl.

The term halo refers to fluoro, chloro, bromo, or iodo, preferably fluoro.

The compounds of the present invention can be converted to their salts, where appropriate, according to conventional methods.

The term "pharmaceutically acceptable salts" refers to acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form. Some of the compounds of this invention may form metal salts such as sodium, potassium, calcium and magnesium salts and these are embraced by the term "pharmaceutically acceptable salts".

The compounds of formula I of this invention contain a chiral center at α-position of hydroxamic acids, as such there exist two enantiomers or a racemic mixture of both. This invention relates to both the enantiomers, as well as mixtures containing both the isomers. In addition, depending on the substituents, additional chiral centers and other isomeric forms may be present in any of the $R^1$ or $R^2$ groups, and this invention embraces all possible stereoisomers and geometric forms in this group.

$R^1$ and $R^2$ are preferably phenyl, 4-methylphenyl, 4-methoxyphenyl, 4-fluorophenyl.

Preferred compounds of this invention are as follows:
a. N-Hydroxy-2,4-bis-[[4-methylphenylsulfonyl]amino] butanamide,
b. (R)-N-Hydroxy-2,4-bis-[[4-methylphenylsulfonyl] amino] butanamide,
c. (S)-N-Hydroxy-2,4-bis-[[4-methylphenylsulfonyl]amino] butanamide,
d. N-Hydroxy-2,3-bis-[[4-methylphenylsulfonyl]amino] propionamide,
e. N-Hydroxy-2,4-bis-[[4-fluorophenylsulfonyl]amino] butanamide,
f. (S)-N-Hydroxy-2,4-bis-[[phenylsulfonyl]amino] butanamide,
g. N-Hydroxy-2,5-bis-[[4-methylphenylsulfonyl]amino] valeramide,
h. N-Hydroxy-2,4-bis-[[4-methoxyphenylsulfonyl]amino] butanamide,
i. N-Hydroxy-4-[(4-methylphenylsulfonylamino)-2-(4-methoxyphenylsulfonylamino)] butanamide,
j. N-Hydroxy-4-[(4-methoxyphenylsulfonylamino)-2-(4-methylphenylsulfonylamino)] butanamide,
k. N-Hydroxy-4-[(4-fluorophenylsulfonylamino)-2-(4-methylphenylsulfonylamino)] butanamide,
l. N-Hydroxy-4-[4-methylphenylsulfonylamino)-2-(4-methoxyphenylsulfonylamino)] butanamide, and
m. N-Hydroxy-4-[(4-fluorophenylsulfonylamino)-2-(4-methoxyphenylsulfonylamino)] butanamide.

The compounds of this invention can be prepared in one of two ways according to the process discussed below. When the two sulfonamide groups are identical, the procedures outlined in Scheme A are utilized. When the sulfonamide groups are different, then the procedures outlined in Scheme B are used.

As shown in Scheme A, bis-sulfonamide 2 is prepared from amino acid 1 by the procedures described in *J. Am. Chem. Soc.*, Vol. 59, p 1116 (1937). In brief, exposure of amino acid 1 to at least two equivalents of the desired sulfonyl chloride in the presence of 1N NaOH gives bis-sulfonamide 2. The starting amino acids 1 are either commercially available or can be conveniently prepared following the procedure of *J. Chem. Soc.*, p 1564 (1939). Reaction of bis-sulfonamide 2 with a peptide coupling reagent such as 1-(3-dimethylaminopropyl)-3-ethylcarbodiimide hydrochloride (EDC) or 1,1'-carbonyldiimidazole (CDI) in the presence of O-benzylhydroxylamine hydrochloride, 4-methylmorpholine and a catalyst such as 1-hydroxybenzotriazole (HOBT) provides protected hydroxamate 3. Occasionally cyclic sulfonamide 4 is isolated as a by-product. In this reaction, either DMF or DMF/$CH_2Cl_2$ are typically used as a solvent. Cyclic sulfonamide 4 can be readily converted to protected hydroxamate 3 by refluxing it with O-benzylhydroxylamine and acetonitrile. Hydrogenation of protected hydroxamate 3 using Pearlman's catalyst in methanol or ethanol provides the desired bis-sulfonamide hydroxamate 5.

When it is desired to have different sulfonamide groups, the procedures in Scheme B are utilized. Following the procedures described in *Chem. Communs.*, Vol. 21, p. 770 (1956), the diamino acid 1 is protected as a copper complex by heating 2,4-diaminobutyric acid dihydrochloride and copper (II) carbonate. The deep blue copper complex solution is reacted with $R_1SO_2Cl$ using sodium bicarbonate in acetone to give the 4 sulfonylamino derivative. This copper complex in 2N hydrochloric acid is then deprotected with hydrogen sulfide to afford the mono-4-$R_1SO_2NH$-2-amino acid 6, see *Collection Chem. Commun.*, Vol. 24, p. 3449 (1959) and *J. Biol. Chem.*, Vol. 220, p. 265 (1956)], which is reacted with $R_2SO_2Cl$ as described in Scheme A to yield the desired compounds 10.

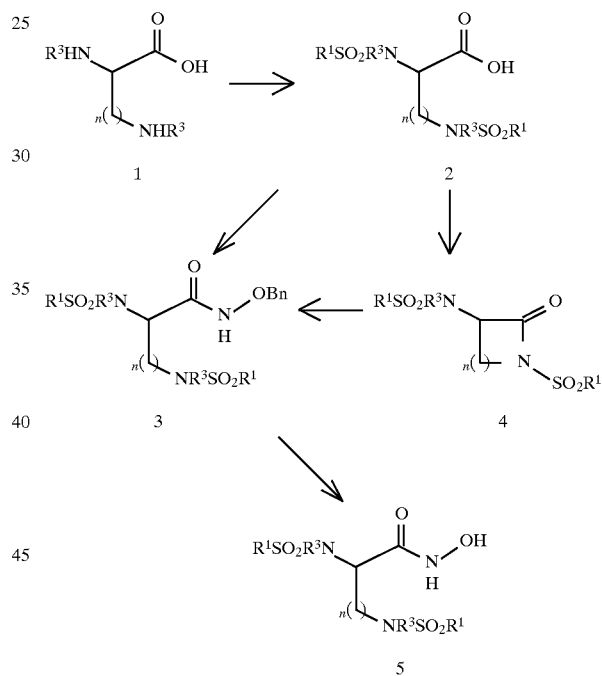

SCHEME A

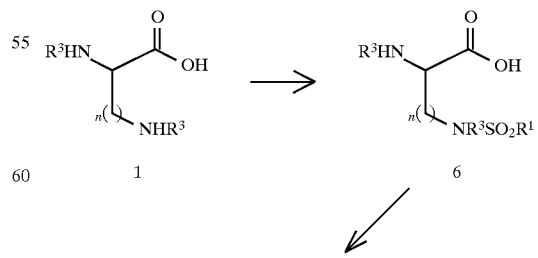

SCHEME B

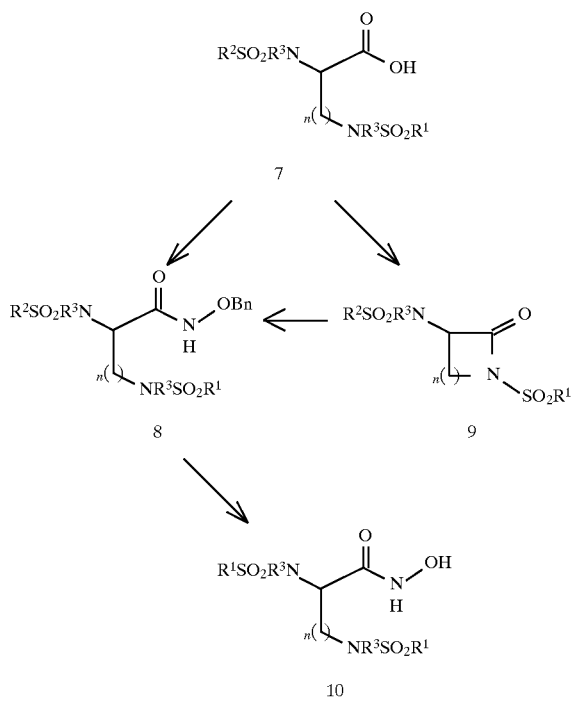

-continued
SCHEME B

The pharmaceutical compositions of this invention may be prepared by combining the compounds of formula I of this invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical composition is provided by employing conventional techniques. Preferably the composition is in unit dosage form containing an effective amount of the active component, that is, the compounds of formula I according to this invention.

The quantity of active component, that is the compounds of formula I according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating a patient, suffering from or susceptible to diseases involving connective tissue degradation, or inhibiting various enzymes from the matrix metalloproteinase family, including collagenase, stromelysin, and gelatinase. The compounds or pharmaceutical compositions thereof will be administered orally, parenterally and/or topically at a dosage to obtain and maintain a concentration, that is, an amount, or blood-level of active component in the patient undergoing treatment which will be effective to inhibit such enzymes. Generally, an effective amount of the active compound will be in the range of about 0.1 to about 100 mg/kg. It is to be understood that the dosages may vary depending upon the requirements of the patient, the severity of connective tissue degradation being treated, and the particular compounds being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of the present invention inhibit various enzymes from the matrix metalloproteinase family, including collagenase, stromelysin, and gelatinase, and hence are useful for the treatment of matrix metallo endoproteinase diseases such as osteoarthritis, rheumatoid arthritis, septic arthritis, osteopenias such as osteoporosis, tumor metastasis, invasion and growth, periodontitis, gingivitis, corneal epidermal ulceration, gastric ulceration, and other diseases related to connective tissue degradation. Such diseases and conditions are well known and readily diagnosed by physician of ordinary skill.

Pharmaceutical compositions for parenteral administration will generally contain a pharmaceutically acceptable amount of the compounds according to formula I as a soluble salt (acid addition salt or base salt) dissolved in a pharmaceutically acceptable liquid carrier such as; for example, water-for-injection and a suitably buffered isotonic solution having a pH of about 3.5–6. Suitable buffering agents include; for example, trisodium orthophosphate, sodium bicarbonate, sodium citrate, N-methylglucamine, L(+)-lysine and L(+)-arginine, to name a few. The compounds according to formula I generally will be dissolved in the carrier in an amount sufficient to provide a pharmaceutically acceptable injectable concentration in the range of about 1 mg/ml to about 400 mg/ml. The resulting liquid pharmaceutical composition will be administered so as to obtain the above-mentioned inhibitory effective amount of dosage. The compounds of formula I according to this invention are advantageously administered orally in solid and liquid dosage forms.

The compounds and their preparations of the present invention will be better understood in connection with the following examples, which are intended as an illustration of and not a limitation upon the scope of the invention.

EXAMPLE 1

Preparation of N-Hydroxy-2,4-bis-[[4-methylphenylsulfonyl]amino] butanamide.

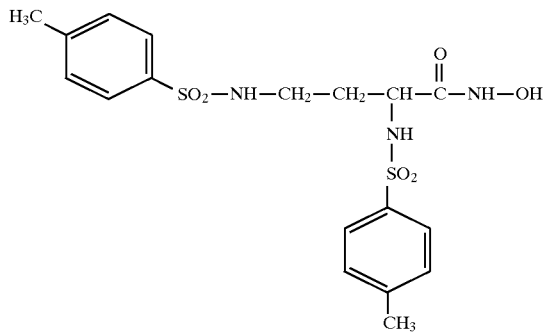

Step 1. Preparation of 2,4-bis-[[4-methylphenylsulfonyl]amino]butyric acid.

To a solution of 5.00 g (26.2 mmol) of 2,4-diaminobutyric acid dihydrochloride and 130 mL (130 mmol) of 1N sodium hydroxide at room temperature is added, in one portion, a solution of 11.0 g (57.6 mmol) of p-toluenesulfonyl chloride in 130 mL of ether. The two layers are stirred for 16 hours at room temperature. The ether layer is separated and the aqueous layer acidified to pH 2. The solid is collected, washed with water, air dried, and dried at 50° C. under high vac. The product is crystallized from isopropyl alcohol/pentane to give 4.33 g of the title compound (mp 187°–188° C.).

IR (cm$^{-1}$) 2924, 1168, 1335, 2754, 2855, 3299, 1092, 2869, 1712; $^1$H NMR (DMSO) 1.64, 1.71, 2.34, 2.37, 2.62, 3.66, 7.30, 7.36, 7.51, 7.58, 7.98.

Step 2. 1-[(4-Methylphenyl)sulfonyl]-4-[(4-methylphenyl)sulfonamide]-2-pyrrolidone.

A mixture of 1.00 g (2.35 mmol) of 2,4-bis-[[4-methylphenylsulfonyl]amino]butyric acid and 0.500 g (3.09 mmol) of 1,1'-carbonyldiimidazole in 15 mL of dry acetone is stirred for 16 hours at room temperature. The acetone is evaporated, water added, the solid collected and air dried. The solid is crystallized from ethyl acetate/methanol/pentane to give 0.90 g of the title compound (mp 193°–194° C.).

IR (cm$^{-1}$) 2924, 1165, 2954, 2855, 1742, 659, 1357, 1141, 1086, 1124; $^1$H NMR (CDCl$_3$) 2.03, 2.42, 2.44, 2.55, 3.65, 3.75, 3.90, 5.09, 7.32, 7.72, 7.89.

Step 3. Preparation of N-Hydroxy-2,4-bis-[[4-methylphenylsulfonyl]amino] butanamide.

A mixture of 0.500 g (1.22 mmol) of 1-[(4-methylphenyl)sulfonyl]-4-[(4-methylphenyl)sulfonamide]-2-pyrrolidone and 1.00 g (8.13 mmol) of O-benzylhydroxylamine in 10 mL of acetonitrile is heated at reflux for 2 days. The solvent is evaporated and the residue partitioned between ethyl acetate and 10% hydrochloric acid. The ethyl acetate layer is extracted with brine, saturated sodium bicarbonate, and brine. The ethyl acetate layer is dried over magnesium sulfate, filtered and concentrated. The product is purified by preparative TLC to give O-benzylhydroxamic acid intermediate.

The O-benzylhydroxamic acid intermediate (0.50 g, 0.94 mmol) and 0.10 g of Pearlman's catalyst in 75 ml of methanol is hydrogenated at 5 psi for 2.5 hours. The mixture is filtered through celite, the filtrate evaporated, and the product dried in vacuo to give 0.395 g of the title compound.

$^1$H NMR (CDCl$_3$) 1.88, 2.32, 2.35, 4.01, 7.21, 7.7; MS m/z [MH$^+$] 442.

EXAMPLE 2

Preparation of (R)-N-Hydroxy-2,4-bis-[[4-methylphenylsulfonyl]amino] butanamide.

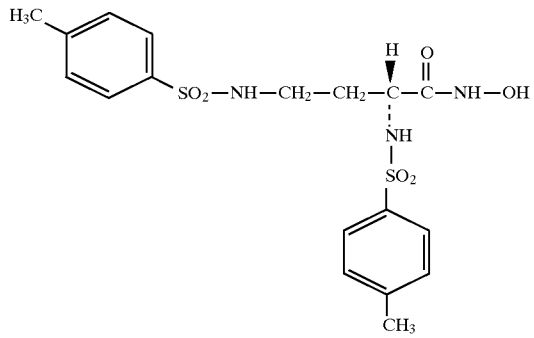

Following the general procedure of Examples 1 and making non-critical variations but starting with (R)-2,4-diaminobutyric acid, the title compound is obtained (mp 152°–153° C.).

$[\alpha]_D$=–8° (DMSO); $^1$H NMR (DMSO) 1.54, 2.35, 2.37, 3.3, 7.28–7.36, 7.57; MS [MH$^+$] m/z 442.

EXAMPLE 3

Preparation of (S)-N-Hydroxy-2,4-bis-[[4-methylphenylsulfonyl]amino] butanamide.

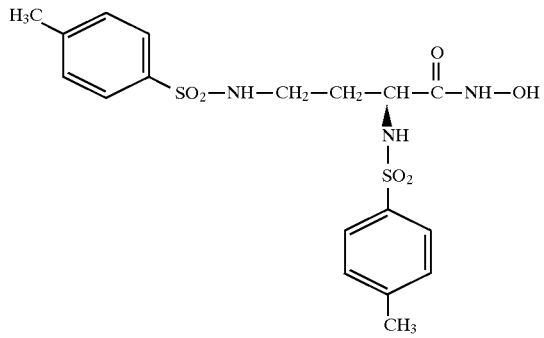

Following the general procedure of Examples 1 and making non-critical variations but starting with (S)-2,4-diaminobutyric acid, the title compound is obtained:

$^1$H NMR (DMSO) 2.6, 2.8, 2.35, 2.37, 7.31, 7.39, 7.58; MS [MH$^+$] m/z 442.

EXAMPLE 4

Preparation of N-Hydroxy-2,3-bis-[[4-methylphenylsulfonyl]amino] propionamide.

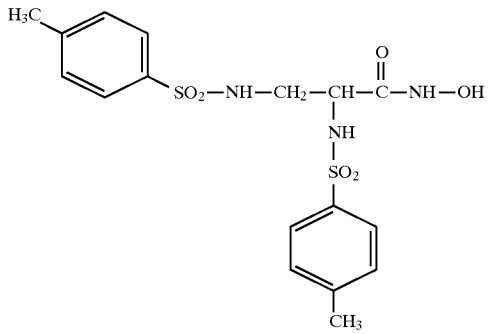

Following the general procedure of Examples 1 and making non-critical variations but starting with 2,3-diaminopropionic acid, the title compound is obtained.

IR (cm$^{-1}$) 2924, 1162, 2954, 2855, 3257, 3276, 2868, 1642, 1330, 3292, 1458; $^1$H NMR (DMSO) 2.36, 2.71, 3.71, 7.32, 7.48, 7.62, 7.9, 8.92, 11.0; MS [MH$^+$] m/z 428.

EXAMPLE 5

Preparation of N-Hydroxy-2,4-bis-[[4-fluorophenylsulfonyl]amino] butanamide.

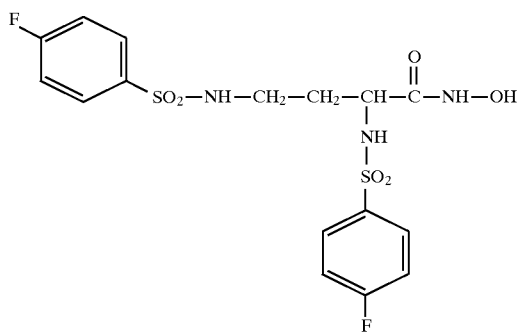

Following the general procedure of Examples 1 and making non-critical variations but starting with 2,4-diaminobutyric acid, the title compound is obtained.

IR (cm$^{-1}$) 1153, 1168, 1495, 1659, 1092, 1592, 1330, 840, 1293, 1239; $^1$H NMR (DMSO) 1.55, 3.53, 7.3–7.45, 7.84; MS [MH$^+$] m/z 450.

EXAMPLE 6

Preparation of (S)-N-Hydroxy-2,4-bis-[[phenylsulfonyl]amino] butanamide.

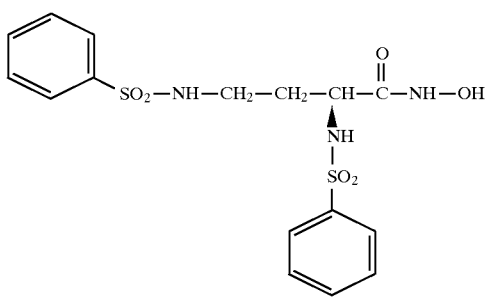

Following the general procedure of Examples 1 and making non-critical variations but starting with (S)-2,4-diaminobutyric acid, the title compound is obtained:

IR (cm$^{-1}$) 2924, 2955, 2855, 1158, 3257, 2868, 1323, 1451, 1328, 1643; $^1$H NMR (DMSO) 1.55, 2.57, 3.51, 7.47–7.80; MS [MH$^+$] m/z 414.

EXAMPLE 7

Preparation of N-Hydroxy-2,5-bis-[[4-methylphenylsulfonyl]amino] valeramide.

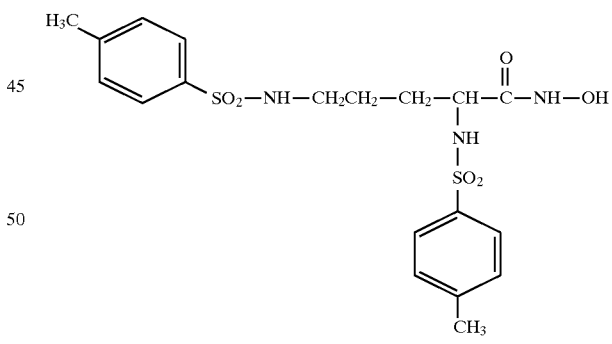

Following the general procedure of Examples 1 and making non-critical variations but starting with ornithine, the title compound is obtained:

IR (cm$^{-1}$) 2924, 1159, 2955, 2855, 3266, 2869, 1329, 1653, 1314, 1307; $^1$H NMR (DMSO) 1.26, 2.36, 3.45, 7.32, 7.62, 7.68; MS [MH$^+$] m/z 456.

EXAMPLE 8

Preparation of N-Hydroxy-2,4-bis-[[4-methoxyphenylsulfonyl]amino] butanamide.

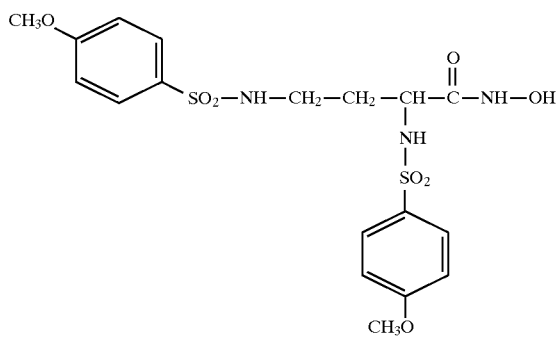

Following the general procedure of Examples 1 and 2 and making non-critical variations but starting with 2,4-diaminobutyric acid, the title compound is obtained.

IR (cm$^{-1}$) 2926, 1155, 2954, 2855, 2869, 1262, 1597, 1499, 1094, 1462, 1324, 1302;
$^1$H NMR (DMSO) 1.54, 3.48, 3.81, 3.82, 7.01, 7.07, 7.33, 7.62, 8.83; MS [MH$^+$] m/z 474.

EXAMPLE 9

Preparation of N-Hydroxy-4-[(4-methylphenylsulfonylamino)-2-(4-methoxyphenylsulfonylamino)]butanamide.

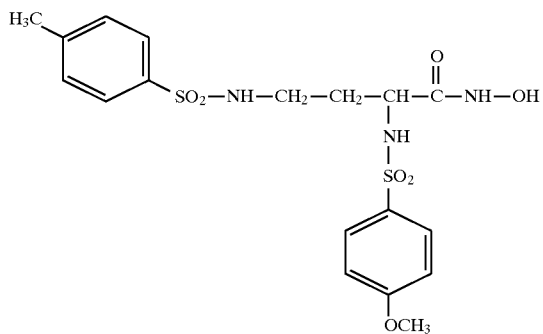

Step 1. Preparation of 2-(4-Methoxyphenylsulfonylamino)-4-(4-methylphenylsulfonylamino)butyric acid.

A mixture of 5.0 g (26 mmol) of 2,4-diaminobutyric acid dihydrochloride, 10 g of copper (II) carbonate and 2.2 g (36 mmol) of sodium bicarbonate in 100 mL of water is stirred at reflux for 2 hours. The reaction mixture is filtered and solid washed with water. The volume of the filtrate is adjusted to 125 mL. Twenty-five milliliters of the blue copper complex solution is reacted with 0.44 g (5.2 mmol) of sodium bicarbonate and 0.60 g (3.1 mmol) of p-toluenesulfonyl chloride in 15 mL of acetone. The reaction is stirred overnight and the solid collected, washed with hot water, ethanol, ether, and air dried to give 1.05 g of a blue solid. This solid, in 2N hydrochloric acid solution, is treated with hydrogen sulfide to form copper sulfide and the 2-amino-4-(4-methylphenylsulfonylamino)butyric acid. The solution is adjusted to pH 6 and cooled at 5° C. to yield 0.5 g of the butyric acid, which is crystallized from ethyl acetate/methanol to give the title compound. (mp 128°–129° C.). For other compounds, the 2N hydrochloric acid solution is concentrated to afford the free 2-amino acid hydrochloride.

$^1$H NMR (DMSO) 1.67, 1.77, 2.36, 2.83), 3.06, 7.36, 7.64; MS m/z [MH$^+$] 272.325.

A mixture 0.50 (1.8 mmol) of the above butyric acid, 4 mL (4 mmol) of 1N sodium hydroxide, and 0.43 g (2.0 mL) of 4-methoxyphenylsulfonyl chloride in 10 mL of ether is stirred for 1–2 days. The ether layer is separated and aqueous layer is acidified with 12N hydrochloric acid to pH 1–2 to yield the product which is filtered, washed with water, and air dried. Crystallization from ethyl acetate/methanol/hexane provides the title compound as a solid (mp 187° C.).

$^1$H NMR (DMSO) 1.65, 2.36, 2.63, 3.59, 3.80, 7.0, 7.35, 7.62. MS m/z [MH$^+$] 442.51.

Step 2. Preparation of N-Hydroxy-4-[(4-methylphenylsulfonylamino)-2-(4-methoxyphenylsulfonylamino)]butanamide.

Following the general procedure of Example 1 and making non-critical variations but starting with the product of Example 9, Step 1, the title compound is obtained.

EXAMPLE 10

Biological Activity Test

Inhibitory activity is evaluated in one or more of the MMP enzymes (stromelysin, gelatinase, and collagenase) in vitro using particle concentration fluorescence assay. An inhibitor binds to MMP enzymes which prevents the degradation of a substrate by stromelysin, gelatinase, or collagenase. The substrate has attached to it a fluorescein and a biotin moiety. The intact substrate then binds to an avidin-coated particle via the biotin moiety. Once the particle is washed and dried, a fluorescent signal is generated since the fluorescent group is attached to the particle. Without an inhibitor present, the substrate is degraded by MMP enzymes and the fluorescein group is removed, therefore, no fluorescent signal can be detected. Testing compounds are dissolved in DMSO to the desired concentration, then the solutions are diluted to 1:5 with MMP buffer (50 mM Tris-HCl, pH 7.5; 150 mM NaCl; 0.02% NaN$_3$). Serial two-fold dilutions of each compound are prepared. A concentrated, activated enzyme solution is transferred into each plate of the testing compounds, and the mixture is incubated at room temperature for 15 minutes. Thawed MMP substrate is then added into all plates, and the plates are incubated in the dark for 1–3 hours at room temperature. At this point, the substrate mixture is mixed with 0.1% avidin-coated polystyrene particles. After 15 minutes, the fluorescence values are measured following filtration and washing of the beads. Ki values are then calculated. Inhibitory data for the compounds of this invention are shown in TABLE 1. Compounds with lower Ki values are expected to be more effective as MMP inhibitors. It is expected that a compound with a Ki less than 15 $\mu$M against stromelysin will display therapeutic effects in connective tissue disorders.

TABLE 1

| MMP Inhibition Constants (Ki, $\mu$M) of the Compounds of the Invention | | | |
|---|---|---|---|
| Example No. | Stromelysin Ki ($\mu$M) | Collagenase, Ki ($\mu$M) | Gelatinase Ki ($\mu$M) |
| 1 | 0.0024 | 0.048 | 0.00094 |
| 2 | 0.0032 | 0.043 | 0.0013 |
| 3 | 0.048 | 0.84 | 0.035 |
| 4 | 0.844 | 0.449 | 0.02 |
| 5 | 0.045 | 0.06 | 0.016 |
| 6 | 2 | 3 | 0.284 |

TABLE 1-continued

| | MMP Inhibition Constants (Ki, μM) of the Compounds of the Invention | | |
|---|---|---|---|
| Example No. | Stromelysin Ki (μM) | Collagenase, Ki (μM) | Gelatinase Ki (μM) |
| 7 | 0.107 | 0.57 | 0.0051 |
| 8 | 0.0012 | 0.093 | 0.0007 |

We claim:

1. A compound of formula I

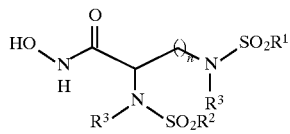

or pharmaceutically acceptable salts thereof wherein
$R^1$ and $R^2$ are the same or different and are
   a) $C_{1-10}$ alkyl,
   b) phenyl,
   c) hetero-aryl, or
   d) phenyl substituted with $C_{1-4}$ alkyl, $OR^3$, $NHR^3$, $CONHR^3$, $NHCOR^3$, $SO_2NHR^3$, or halo;
$R^3$ is
   a) H, or
   b) $C_{1-4}$ alkyl; and
n is 1, 2, 3, 4, 5, or 6.

2. A compound of claim 1 wherein $R^1$ and $R^2$ are selected from the group consisting of phenyl, 4-methylphenyl, 4-methoxyphenyl, 4-fluorophenyl.

3. A compound of claim 1 which is
a. N-Hydroxy-2,4-bis-[[4-methylphenylsulfonyl]amino] butanamide,
b. (R)-N-Hydroxy-2,4-bis-[[4-methylphenylsulfonyl] amino] butanamide,
c. (S)-N-Hydroxy-2,4-bis-[[4-methylphenylsulfonyl]amino] butanamide,
d. N-Hydroxy-2,3-bis-[[4-methylphenylsulfonyl]amino] propionamide,
e. N-Hydroxy-2,4-bis-[[4-fluorophenylsulfonyl]amino] butanamide,
f. (S)-N-Hydroxy-2,4-bis-[[phenylsulfonyl]amino] butanamide,
g. N-Hydroxy-2,5-bis-[[4-methylphenylsulfonyl]amino] valeramide,
h. N-Hydroxy-2,4-bis-[[4-methoxyphenylsulfonyl]amino] butanamide, or
i. N-Hydroxy-4-[(4-methylphenylsulfonylamino)-2-(4-methoxyphenylsulfonylamino)] butanamide,
j. N-Hydroxy-4-[(4-methoxyphenylsulfonylamino)-2-(4-methylphenylsulfonylamino)] butanamide,
k. N-Hydroxy-4-[(4-fluorophenylsulfonylamino)-2-(4-methylphenylsulfonylamino)] butanamide,
l. N-Hydroxy-4-[4-methylphenylsulfonylamino)-2-(4-methoxyphenylsulfonylamino)] butanamide, or
m. N-Hydroxy-4-[(4-fluorophenylsulfonylamino)-2-(4-methoxyphenylsulfonylamino)] butanamide.

4. A compound of claim 1 which is
a. N-Hydroxy-2,4-bis-[[4-methylphenylsulfonyl]amino] butanamide,
b. (R)-N-Hydroxy-2,4-bis-[[4-methylphenylsulfonyl] amino] butanamide, or
c. N-Hydroxy-2,4-bis-[[4-methoxyphenylsulfonyl]amino] butanamide.

5. A compound of claim 1 wherein n is 2.

6. A method of inhibiting excess matrix metalloproteinase which comprises administering to a patient in need thereof an effective amount of a compound of claim 1.

7. A method of claim 6 wherein matrix metalloproteinases comprises stromelysin, collagenase, and gelatinase.

8. A method of treating a human suffering from or susceptible to diseases involving connective tissue degradation which comprises administering to a patient in need thereof an effective amount of a compound of claim 1.

9. A method of claim 6 wherein the diseases related to connective tissue degradation are osteoarthrits, rheumatoid arthritis, septic arthritis, osteopenias such as osteoporosis, tumor metastasis (invasion and growth), periodontitis, gingivitis, corneal ulceration, dermal ulceration, gastric ulceration and other diseases related to connective tissue degradation.

10. The method of claim 6 wherein the effective amount of the compound of claim 1 is administered orally, parenterally, or topically in a pharmaceutical composition.

11. The method of claim 8 wherein the effective amount of the compound of claim 1 is administered orally, parenterally, or topically in a pharmaceutical composition.

12. The method of claim 6 or 8 wherein said compound is administered in an amount of from about 0.1 to about 100 mg/kg of body weight/day.

13. A pharmaceutical composition which comprises an amount of the compound of claim 1 effective to inhibit excess matrix metalloproteinase and a pharmaceutically acceptable carrier.

* * * * *